United States Patent
Mitsushima et al.

(10) Patent No.: US 10,202,698 B2
(45) Date of Patent: Feb. 12, 2019

(54) DEVICE FOR MANUFACTURING ORGANIC HYDRIDE

(71) Applicants: YOKOHAMA NATIONAL UNIVERSITY, Yokohama, Kanagawa (JP); DE NORA PERMELEC LTD, Fujisawa, Kanagawa (JP)

(72) Inventors: Shigenori Mitsushima, Yokohama (JP); Yasutomo Takakuwa, Yokohama (JP); Yoshinori Nishiki, Fujisawa (JP); Akihiro Kato, Fujisawa (JP); Akiyoshi Manabe, Fujisawa (JP); Yasushi Sato, Tokyo (JP); Kota Miyoshi, Tokyo (JP); Kojiro Nakagawa, Tokyo (JP); Shinji Oshima, Tokyo (JP)

(73) Assignees: Yokohama National University, Yokohama (JP); DE NORA PERMELEC LTD, Fujisawa (JP)

( * ) Notice: Subject to any disclaimer, the term of this patent is extended or adjusted under 35 U.S.C. 154(b) by 0 days.

(21) Appl. No.: 15/129,670

(22) PCT Filed: Mar. 24, 2015

(86) PCT No.: PCT/JP2015/058824
§ 371 (c)(1),
(2) Date: Sep. 27, 2016

(87) PCT Pub. No.: WO2015/146944
PCT Pub. Date: Oct. 1, 2015

(65) Prior Publication Data
US 2017/0130344 A1    May 11, 2017

(30) Foreign Application Priority Data
Mar. 28, 2014 (JP) .................... 2014-069716

(51) Int. Cl.
*C25B 9/08* (2006.01)
*C25B 9/16* (2006.01)
(Continued)

(52) U.S. Cl.
CPC ............... *C25B 3/04* (2013.01); *B01J 19/088* (2013.01); *C07C 5/10* (2013.01); *C25B 1/10* (2013.01);
(Continued)

(58) Field of Classification Search
CPC .... C25B 9/08; C25B 1/10; C25B 9/00; C25B 3/00; C25B 9/16; C25B 9/206
(Continued)

(56) References Cited

U.S. PATENT DOCUMENTS

2013/0313127 A1  11/2013  Sato
2014/0144774 A1   5/2014  Hirashige
2014/0326610 A1  11/2014  Sato

FOREIGN PATENT DOCUMENTS

CA    2859936    7/2013
CA    2861209    8/2013
(Continued)

OTHER PUBLICATIONS

Supplementary European Search Report for EP 15769674.
(Continued)

*Primary Examiner* — Zulmariam Mendez
(74) *Attorney, Agent, or Firm* — Jeremy Howard; Howard IP Law (57) ABSTRACT

A device for producing an organic hydride 10 of an aspect of the present invention has an electrochemical cell provided with an anode 12 on a surface of an electrolyte membrane 11 and a cathode including a cathode catalyst layer 13 and a cathode diffusion layer 14 on another surface of the electrolyte membrane 11. A gap is provided between the anode (Continued)

12 and the electrolyte membrane 11. The anode 12 has a network structure with an aperture ratio of 30 to 70%, and has an electrical supply supporting material formed of an electronic conductor and the electrode catalyst held by the electrical supply supporting material.

4 Claims, 3 Drawing Sheets

(51) Int. Cl.
    *C25B 3/00*     (2006.01)
    *C25B 3/04*     (2006.01)
    *C07C 5/10*     (2006.01)
    *C25B 11/03*     (2006.01)
    *C25B 15/08*     (2006.01)
    *C25B 1/10*     (2006.01)
    *C25B 9/10*     (2006.01)
    *B01J 19/08*     (2006.01)
    *C25B 9/00*     (2006.01)
    *C25B 11/04*     (2006.01)
    *C25B 13/08*     (2006.01)

(52) U.S. Cl.
    CPC ............... *C25B 9/00* (2013.01); *C25B 9/10* (2013.01); *C25B 11/03* (2013.01); *C25B 11/0405* (2013.01); *C25B 11/0484* (2013.01); *C25B 13/08* (2013.01); *C25B 15/08* (2013.01); *B01J 2219/0809* (2013.01); *B01J 2219/0815* (2013.01); *B01J 2219/0824* (2013.01); *B01J 2219/0877* (2013.01); *C07C 2601/14* (2017.05); *Y02E 60/366* (2013.01)

(58) Field of Classification Search
    USPC .................................................. 204/252, 280
    See application file for complete search history.

(56) References Cited

FOREIGN PATENT DOCUMENTS

| | | |
|---|---|---|
| EP | 2660356 A1 | 11/2013 |
| JP | 49-56952 A | 6/1974 |
| JP | 58-91178 A | 5/1983 |
| JP | 2012-72477 | 4/2012 |
| JP | 2012-107331 A | 6/2012 |
| WO | 2013/111585 A1 | 8/2014 |
| WO | 2016047629 A1 | 3/2016 |
| WO | 2016076277 A1 | 5/2016 |
| WO | 2016080505 A1 | 5/2017 |

OTHER PUBLICATIONS

Chinese Office Action for application 201580016639.1 dated Jun. 11, 2017.
Canadian Office Action for application 2,944,134 dated Oct. 23, 2017.
International Search Report for PCT/JP2015/058824.
Office Action for EP 15769674.1 dated Feb. 22, 2018.
Office Action for CN20150016639.1 dated Jan. 22, 2018.
Introduction to Titanium Electrode, Zhang Zhaoxian etc. Metallurgical Industry Press, pp. 437 to 442, Sep. 30, 2008.
Office Action for CN201580016639.1 dated Jan. 22, 2018.
Introduction to Titanium Electrode, Zhang Zhaoxian etc. Metallurgical Indsutry Press, pp. 437 to 442, Sep. 30, 2008.
Canadian Office Action for Application 2,944,134 dated May 22, 2018.
Office Action for JP 2016-510361 dated Jul. 3, 2018.

DEVICE FOR MANUFACTURING ORGANIC HYDRIDE

The present application is related to PCT Application No. PCT/JP2015/058824, filed on Mar. 24, 2015, and claims priority from Japanese application No. 2014-069716, filed on Mar. 28, 2014, the entirety of each is incorporated herein by reference.

TECHNICAL FIELD

The present invention relates to a device for producing an organic hydride in which hydrogenation of the organic hydride is electrochemically performed.

BACKGROUND ART

While an energy problem has been serious, attention has been paid to renewable energy. However, since the renewable energy such as sunlight and wind power is fluctuated and unevenly distributed, transportation and storage as electric energy are difficult. For this reason, hydrogen is a strong candidate for the transportation and storage of the renewable energy. However, hydrogen is a gas at a normal temperature and a normal pressure and is not suitable for the transportation and storage.

Attention is paid to organic hydrides using hydrocarbons, such as cyclohexane, methyl cyclohexane, and decalin, which are used for transportation and storage of hydrogen. The organic hydrides are a liquid at a normal temperature and a normal pressure, and are easily handled. When the organic hydrides are electrochemically hydrogenated or dehydrogenated, the organic hydrides act as an energy carrier instead of hydrogen to enable storage and transportation.

In conventional production of organic hydrides such as methyl cyclohexane, hydrogen is produced by water electrolysis using renewable energy, and toluene is hydrogenated using a hydrogenation reactor to produce methyl cyclohexane. In an electro-synthesis method, a process can be simplified by direct hydrogenation.

CITATION LIST

Patent Literature

Patent Literature 1: Japanese Patent Application Laid-Open No. 2012-72477

SUMMARY OF INVENTION

Technical Problem

In Patent Literature 1 that describes a conventional device for producing an organic hydride, a solid polymer electrolyte membrane is joined to not only a cathode catalyst but also an anode catalyst. Therefore, Patent Literature 1 has a problem in which an oxygen gas generated on the anode catalyst tends to remain.

The present invention has been made in view of such a problem, and an object of the present invention is to provide a technology capable of suppressing retention of an oxygen gas on an anode catalyst of a device for producing an organic hydride.

Solution to Problem

An aspect of the present invention is a device for producing an organic hydride. The device for producing an organic hydride includes: a solid polymer electrolyte membrane having proton conductivity; a cathode that is provided on a surface of the solid polymer electrolyte membrane and contains an electrolytic-hydrogenation catalyst for reducing a substance to be hydrogenated to produce a hydride; a cathode chamber that accommodates the cathode and into which the substance to be hydrogenated is supplied; an anode that is provided on another surface of the solid polymer electrolyte membrane and contains an electrode catalyst for oxidizing water to produce protons; and an anode chamber that accommodates the anode and into which an electrolytic solution is supplied, and is characterized in that a gap is formed between the anode and the electrolyte membrane.

In the device for producing an organic hydride of the aspect described above, the anode may have a network structure with an aperture ratio of 30 to 70%, and have an electrical supply supporting material formed of an electronic conductor and the electrode catalyst held by the electrical supply supporting material. The anode may have a rhombic aperture shape with a distance between centers in a short direction of 0.1 to 4 mm and a distance between centers in a long direction of 0.1 to 6 mm. Herein, the "short direction" and the "long direction" are terms for discriminating directions, and do not specify the discrimination of directions on the basis of a difference in length. The gap may be 0.02 to 0.2 mm. The electrolytic solution may be sulfuric acid, phosphoric acid, nitric acid, or hydrochloric acid, which has an ion conductance measured at 20° C. of 0.01 S/cm or more.

Proper combinations of the respective components described above can also be included in the scope of the present invention that seeks protection conferred by the present patent application.

Advantageous Effects of Invention

According to the present invention, an oxygen gas is prevented from remaining on an anode catalyst of the device for producing an organic hydride.

DESCRIPTION OF EMBODIMENTS

Hereinafter, an embodiment of the present invention will be described with reference to the drawings.

Figure 1:
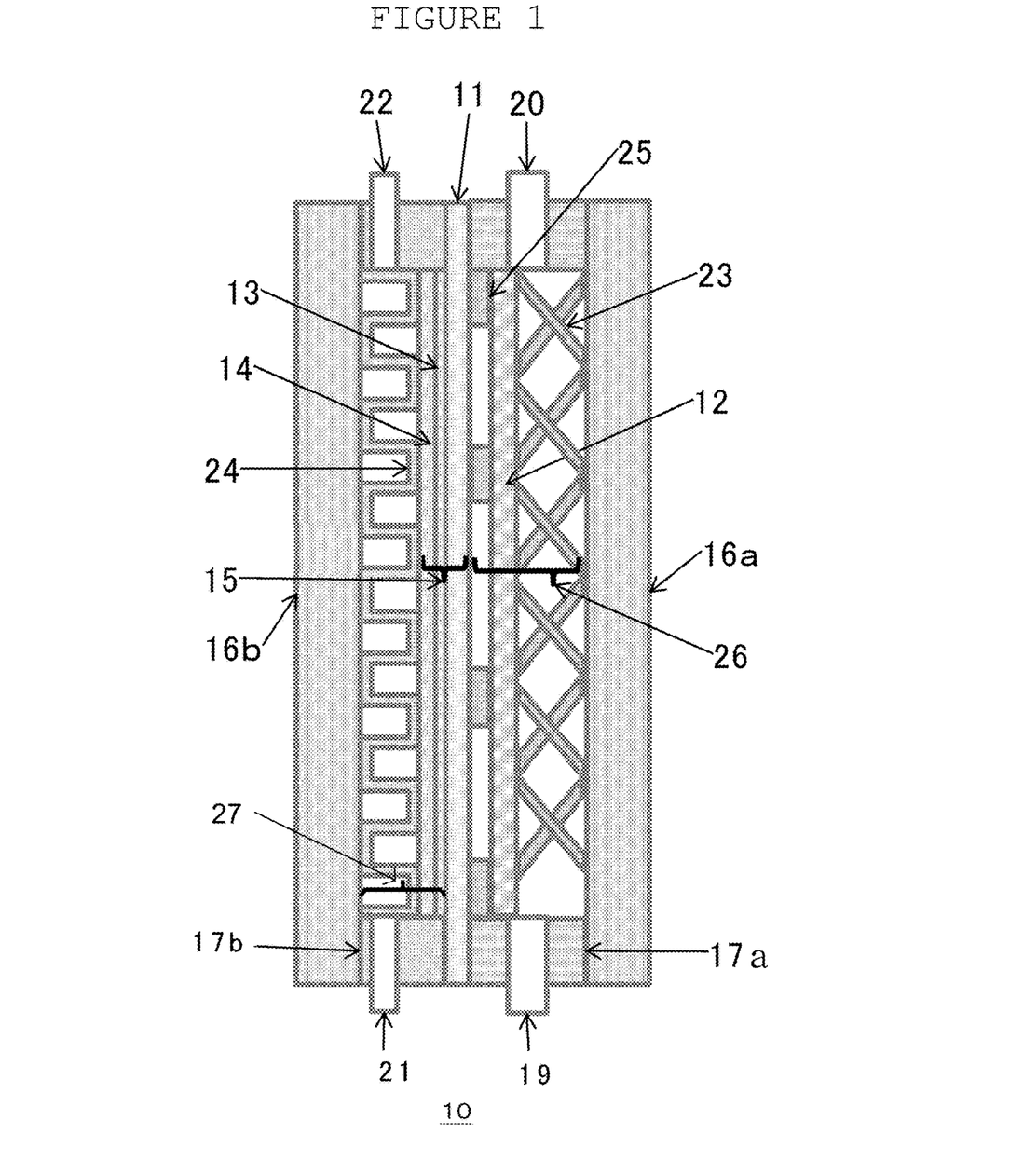
FIG. 1 is a diagram illustrating a schematic configuration of a device for producing an organic hydride according to an embodiment.

FIG. 1 illustrates a diagram of a schematic configuration of a device for producing an organic hydride 10 according to an embodiment. The device for producing an organic hydride 10 has an electrochemical cell provided with an anode 12 on a surface of an electrolyte membrane 11 and a cathode including a cathode catalyst layer 13 and a cathode diffusion layer 14 on another surface of the electrolyte membrane 11. Hereinafter, each part of the device for producing an organic hydride 10 will be described in detail.

The electrolyte membrane 11 is formed of a material (ionomer) having proton conductivity. While protons are selectively conducted, substances are prevented from being mixed or diffused between the cathode and the anode 12. The thickness of the electrolyte membrane 11 is preferably 5 to 300 μm, more preferably 10 to 150 μm, and most preferably 20 to 100 μm. When the thickness of the electrolyte membrane 11 is less than 5 μm, the barrier property of the electrolyte membrane 11 is decreased, and cross-leaking is likely to occur. When the thickness of the electrolyte membrane 11 is more than 500 μm, ion transfer resistance becomes too large. Thus, this is not preferred.

Figure 2:
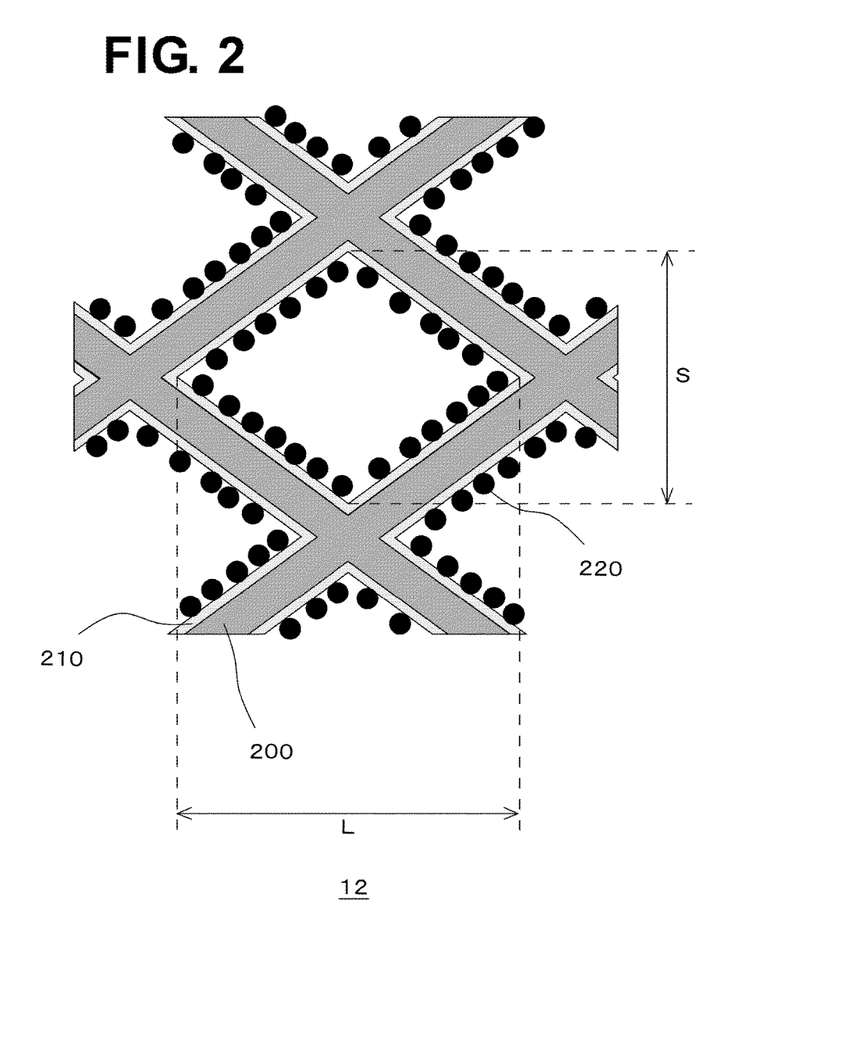
FIG. 2 is a diagram schematically illustrating a structure of an anode.

FIG. 2 is a diagram schematically illustrating a structure of the anode 12. As shown in FIG. 2, the anode 12 has an electrical supply supporting material 200 and an electrode catalyst 220. It is desirable that the electrical supply supporting material 200 be a plate-shaped material having electrical conductivity sufficient to supply a current necessary for electrolysis, and a thickness of a base material of 0.1 mm to 2 mm and a network structure due to necessity for mechanical strength of an electrolysis cell. The aperture ratio of an aperture to the entire surface of the electrical supply supporting material 200 falls within a range of 30 to 70%. When the aperture ratio is less than 30%, an oxygen gas (bubbles) generated on the anode 12 is not rapidly removed. Therefore, cell resistance is increased due to so-called bubble effect. In contrast, when the aperture ratio is 70% or more, bubbles are rapidly removed, but an effective area of an electrode is decreased, and apparent base material electric conductivity is also decreased. Thus, the resistance of the whole cell is increased to decrease the electrolysis performance. It is preferable that the electrical supply supporting material 200 have a rhombic aperture shape with a distance S between centers in a short direction of 0.1 to 4 mm and a distance L between centers in a long direction of 0.1 to 6 mm. When the distance S between centers in the short direction is larger than 4 mm or the distance L between centers in the long direction is larger than 6 mm, the current distribution in the electrolysis cell, particularly in the electrolyte membrane 11 may be made ununiform. Thus, the resistance of the whole cell may be increased to decrease the electrolysis performance. In contrast, when the distance S between centers in the short direction is smaller than 0.1 mm or the distance L between centers in the long direction is smaller than 0.1 mm, the electrolysis performance may be improved, but the thickness of the base material is decreased for certain reasons in terms of processing and handling is made inconvenient. As a countermeasure, the thickness of the electrical supply supporting material 200 may be increased. However, the production cost of the electrical supply supporting material 200 is increased, and as a result, the production cost of the anode 12 is increased, and use thereof in an actual device is difficult.

In order to avoid an increase in resistance due to the bubbles and promote supply of a liquid to be electrolyzed, it is preferable that the anode 12 as a gas-generating electrode be a porous body and have excellent corrosion resistance against an acidic electrolyte. As the electrical supply supporting material 200, an expanded mesh made of titanium is preferably used. It is desirable that the expanded mesh be appropriately smoothened so that the mesh has a three-dimensional structure after mesh processing. When the expanded mesh is used as the electrical supply supporting material 200, the long direction is a direction of a slit during production of the expanded mesh, and the short direction is a direction orthogonal to the slit.

The electrode catalyst 220 is held on a surface of the electrical supply supporting material 200. As the electrode catalyst 220 in which oxygen is generated with the electrode catalyst immersed in an acidic electrolytic solution, a platinum-group noble metal oxide-based catalyst is preferably used. In particular, an iridium oxide-based electrode catalyst material has low voltage loss and excellent durability. It is particularly preferable that the electrode catalyst 220 be an iridium oxide-based electrode catalyst formed with tantalum oxide into a solid solution since an increase in voltage loss in a system in which an organic substance is mixed is small.

When the acidic electrolytic solution comes into contact with the anode 12, a metal used as the electrical supply supporting material 200 of the anode 12, such as titanium, is oxidized to form an insulating film. Therefore, it is preferable that on at least a surface of the electrical supply supporting material 200 into contact with the electrode catalyst 220, a coating 210 of a conductive valve metal such as tantalum or an alloy layer thereof, a noble metal, or a noble metal oxide be formed. Accordingly, conductivity between the electrical supply supporting material 200 and the electrode catalyst 220 can be favorably kept.

Returning back to the description of FIG. 1, a partition plate 16a having electron conductivity is disposed on the outermost portion of the electrochemical cell on a side of the anode 12. The partition plate 16a is, for example, formed of a metal such as titanium.

A spacer 17a is attached between a peripheral portion of surface of the partition plate 16a on the anode 12 side and the electrolyte membrane 11. An anode chamber 26 is a space surrounded by the partition plate 16a, a spacer 17 of side edge of the anode chamber, and the electrolyte membrane 11. The spacer 17a also functions as a sealing material of preventing the acidic electrolytic solution from leaking out of the anode chamber 26, and desirably has electrical insulating properties. Examples of a material for the spacer 17a may include an ethylene tetrafluoride resin.

An acidic electrolytic solution inlet 19 is provided at a lower portion of the spacer 17a, and the acidic electrolytic solution is supplied from the acidic electrolytic solution inlet 19 to the anode chamber 26. Examples of the acidic electrolytic solution may include sulfuric acid, phosphoric acid, nitric acid, and hydrochloric acid, which have an ion conductance measured at 20° C. of 0.01 S/cm or more. When the ion conductance is lower than 0.01 S/cm, an industrially sufficient electrochemical reaction is unlikely to be achieved. An acidic electrolytic solution outlet 20 is provided at an upper portion of the spacer 17a, and the acidic electrolytic solution stored in the anode chamber 26 is discharged out of the system through the acidic electrolytic solution outlet 20.

An anode-supporting elastic body 23 is disposed between the anode 12 and the partition plate 16a, and the anode 12 is pushed onto the electrolyte membrane 11 by the anode-supporting elastic body 23. The anode-supporting elastic body 23 is, for example, formed of an electronic conductor having a plate spring or coil structure. When a structure holding the anode 12 is formed by providing the anode-supporting elastic body 23 between the partition plate 16a and the anode 12 that constitute the anode chamber 26, as described above, a maintenance operation such as replacement of the anode 12 can be facilitated. An anode spacer 25 is provided between the anode 12 and the electrolyte membrane 11. The anode spacer 25 is configured to keep a predetermined gap between the anode 12 and the electrolyte membrane 11. The gap between the anode 12 and the electrolyte membrane 11 is preferably 0.02 mm or more and less than 1.0 mm, and more preferably 0.05 mm or more and 0.5 mm or less.

It is preferable that the anode-supporting elastic body 23 be formed of a material having acid resistance to the acidic electrolytic solution supplied from the acidic electrolytic solution inlet 19 and titanium or titanium alloy be used as a base material. As an elastic body structure constituting the anode-supporting elastic body 23, various types of structures such as types of V-shaped spring, X-cross spring, and cushion coil, and an aggregate of fibers produced by chatter vibration cutting method are considered. In view of contact resistance of each member, the thickness of a material, and the like, are appropriately selected for a necessary contact pressure.

The cathode catalyst layer 13 is formed of a noble metal-supported catalyst and an ionomer having proton conductivity. When the cathode and the electrolyte membrane 11 are joined, a cathode-membrane joined body 15 is formed. In this embodiment, when the cathode and the electrolyte membrane 11 deteriorate, replacement of only the cathode-membrane joined body 15 can decrease a cost necessary for maintenance to the minimum required cost.

The cathode diffusion layer 14 is, for example, formed of carbon paper or carbon cloth. The cathode diffusion layer 14 is in contact with the cathode catalyst layer 13 having a matrix structure in which platinum- or platinum alloy-supported carbon is mixed with a catalyst and a protonically conductive solid electrolyte.

A partition plate 16b having electron conductivity is disposed on the outermost portion of the cathode of the electrochemical cell. The partition plate 16b is, for example, formed of a metal such as stainless.

A spacer 17b is attached between a peripheral portion of the cathode of the partition plate 16b and the electrolyte membrane 11. A cathode chamber 27 is a space surrounded by the partition plate 16b, the spacer 17b, and the electrolyte membrane 11. The spacer 17b also functions as a sealing material of preventing a substance to be hydrogenated and an organic substance containing a hydride from leaking out of the cathode chamber 27, and desirably has electrical insulating properties. Examples of a material for the spacer 17b may include an ethylene tetrafluoride resin.

A substance-to-be-hydrogenated inlet 21 is provided at a lower portion of the spacer 17b, and the substance to be hydrogenated such as toluene is supplied from the substance-to-be-hydrogenated inlet 21 to the cathode chamber 27. A hydride outlet 22 is provided at an upper portion of the spacer 17b, and an organic substance containing a hydride such as methylcyclohexane that is a hydride of toluene is discharged out of the system through the hydride outlet 22.

A cathode support 24 is disposed between the partition plate 16b and the cathode diffusion layer 14. The cathode support 24 receives a pushing force by the anode-supporting elastic body 23, and secures electron conductivity between the partition plate 16b and the cathode diffusion layer 14. The cathode support 24 also forms a flow channel of controlling the flows of the substance to be hydrogenated and the hydride.

According to the device for producing an organic hydride described above, since the anode in which the electrode catalyst is held in the electrical supply supporting material having a network structure designed within such a range that the aperture dimension is appropriate is used, an oxygen gas generated on the electrode catalyst of the anode 12 by electrolysis of water is prevented from remaining. Accordingly, an electrolysis reaction can proceed more smoothly over an extended period of time.

Since the anode spacer 25 is provided between the anode 12 and the electrolyte membrane 11 and configured to keep a predetermined gap between the anode 12 and the electrolyte membrane 11, an oxygen gas generated on the anode 12 is easy to be shifted upward. Therefore, retention of the oxygen gas on the electrode catalyst of the anode 12 can be further suppressed.

EXAMPLES

Hereinafter, examples of the present invention will be described. However, the examples are merely examples for appropriately illustrating the present invention, and not meant to limit the present invention.

Example 1

Example 1 is a structure in accordance with the device for producing an organic hydride (electrolysis cell) illustrated in FIG. 1. Hereinafter, the device for producing an organic hydride of Example 1 will be described in detail.

As an electrolyte membrane, NRE212CS (available from DuPont, thickness: 50 μm) was used. On a surface of the membrane, a cathode catalyst layer was formed by a spray coating method, to form a cathode-electrolyte membrane composite. In the formation of the cathode catalyst layer, ionomer Nafion (registered trademark) dispersion solution DE2020 (available from DuPont) was first added to PtRu/C catalyst TEC61E54E (available from Tanaka Kikinzoku Kogyo, Pt: 23% by weight, Ru: 27% by weight) powder so that a ratio of the dried weight to the weight of carbon in the catalyst was 1:1, whereby an ink for coating was prepared appropriately using a solvent. This ink was applied to the electrolyte membrane by spray coating so that the total weight of Pt and Ru in the catalyst per an electrode area was 0.5 mg/cm$^{-2}$. Subsequently, the solvent component in the ink was dried at 80° C. to obtain the cathode catalyst layer.

To a surface of the cathode catalyst layer, a cathode diffusion layer SGL35BC (available from SGL Carbon AG) that was cut according to the electrode surface was attached, and thermally joined at 120° C. and 1 MPa for 2 minutes, to form a cathode-electrolyte composite.

As a structure in which a cathode partition plate and a cathode support were joined, a carbon-based structure obtained by molding carbon/epoxy resin was used. The cathode support portion of the structure had a plurality of flow channels for liquid flowing on a surface in contact with the cathode diffusion layer. Each of the flow channels had a spacing portion having a width of 1 mm and a flow channel height of 0.5 mm, and a straight shape having a distance between the flow channels of 1 mm. Each of the flow channels was provided parallel to a vertical direction of the device for producing an organic hydride during setting. Both terminals of the flow channels of the structure had a liquid header integrating the plurality of flow channels for supply and discharge of the liquid, and were connected to paths for supply and discharge of an organic substance through the fluid header.

As an anode substrate, an expanded mesh having a distance between centers in a short direction of 3.5 mm, a distance between centers in a long direction of 6.0 mm, a plate thickness of 1.0 mm, a pitch width of 1.1 mm, and an aperture ratio of 42% was used (see Table 1). A surface of the anode substrate was subjected to a dry blast treatment, followed by a washing treatment in a 20% sulfuric acid aqueous solution. After that, the washed surface of the anode substrate was coated so as to have a coating thickness of 2 μm using an arc ion plating device and a target JIS class 1 titanium circular plate of pure titanium at a substrate temperature of 150° C. and a degree of vacuum of $1.0 \times 10^{-2}$ Torr. An operation in which a mixed aqueous solution of iridium tetrachloride/tantalum pentachloride was applied to the thus obtained anode substrate followed by a heat treatment at 550° C. in an electric furnace was repeated a plurality of times. Thus, an electrode catalyst layer formed of a solid solution of iridium oxide and tantalum oxide was formed as an anode so that the weight per an electrode area in terms of Ir metal amount was 12 $g/m^2$.

As an anode-supporting elastic body, an elastic body in which flat springs with a pitch of 10 mm obtained by processing a Ti plate with a thickness of 0.3 mm were arranged was used. On a contact surface of the flat springs with the anode, a slight amount of platinum layer was formed.

These cell members, that is, the cathode support, the cathode-electrolyte membrane composite, an anode spacer, the anode, and the anode-supporting elastic body were layered in this order, and the anode-supporting elastic body was inserted between a partition plate on the anode side and the anode. Thus, the respective layers were pushed by a pushing force from the anode side so that the layers were closely adhered within a fixed cell width. The thickness of the anode spacer, that is, a gap between the electrolyte membrane and the anode was 0.05 mm.

Through a cathode chamber of the device for producing an organic hydride thus obtained, toluene was passed by a riser (upward along a vertical direction). Through a spacing portion (anode chamber) between the anode and the partition plate on the anode side, a 5% sulfuric acid aqueous solution was passed by a riser, similarly. A negative electrode of a constant voltage power supply was connected to the cathode and a positive electrode was connected to the anode. The following electrolysis reaction was performed. A circulation flow rate of each fluid was set so that a linear rate on the cathode side was 1 m/min and a linear rate on the anode side was 3 m/min.

between centers in a short direction of 2.0 mm, a distance between centers in a long direction of 4.0 mm, a plate thickness of 0.6 mm, a pitch width of 0.6 mm, and an aperture ratio of 45% was used (see Table 1).

Example 3

A device for producing an organic hydride of Example 3 had the same configuration as in Example 2 except that a gap between the electrolyte membrane and the anode was 0.2 mm (see Table 1).

Example 4

A device for producing an organic hydride of Example 4 had the same configuration as in Example 1 except that as an anode substrate, an expanded mesh having a distance between centers in a short direction of 6.0 mm, a distance between centers in a long direction of 10 mm, a plate thickness of 0.6 mm, a pitch width of 1.0 mm, and an aperture ratio of 60% was used, and a gap between the electrolyte membrane and the anode was 0.02 mm (see Table 1).

Comparative Example 1

A device for producing an organic hydride of Comparative Example 1 had the same configuration as that of the device for producing an organic hydride of Example 1 except that an electrode in which a Ti fiber-sintered sheet available from Bekaert Japan was coated with $IrO_2$ was used as an anode. The porosity of the Ti fiber-sintered sheet was 65%, and the average pore diameter was about 30 mm.

Comparative Example 2

A device for producing an organic hydride of Comparative Example 2 had the same configuration as in Example 1 except that the anode spacer was not provided and the electrolyte membrane and the anode were closely adhered (see Table 1).

TABLE 1

| | Expanded Mesh | | | | | | | |
| --- | --- | --- | --- | --- | --- | --- | --- | --- |
| | Distance Between Centers in Short Direction | Distance Between Centers in Long Direction | Thickness | Pitch Width | Aperture Ratio | Ion Conductance | Gap | Current Density After 60 Minutes (Applied Voltage 1.7 V) |
| Example 1 | 3.5 mm | 6.0 mm | 1.0 mm | 1.1 mm | 42% | 0.25 S/cm | 0.05 mm | 130 mA |
| Example 2 | 2.0 mm | 4.0 mm | 0.6 mm | 0.6 mm | 45% | 0.25 S/cm | 0.05 mm | 120 mA |
| Example 3 | 2.0 mm | 4.0 mm | 0.6 mm | 0.6 mm | 45% | 0.25 S/cm | 0.2 mm | 110 mA |
| Example 4 | 6.0 mm | 10 mm | 0.6 mm | 1.0 mm | 60% | 0.25 S/cm | 0.02 mm | 90 mA |
| Comparative Example 1 | — | — | — | — | 65% (Porosity) | 0.25 S/cm | — | 80 mA (Applied Voltage 1.75 V) |
| Comparative Example 2 | 3.5 mm | 6.0 mm | 1.0 mm | 1.1 mm | 42% | 0.25 S/cm | None | 50 mA |
| Comparative Example 3 | 3.0 mm | 3.5 mm | 1.0 mm | 1.1 mm | 20% | 0.25 S/cm | 0.05 mm | 50 mA |
| Comparative Example 4 | 8.0 mm | 12 mm | 1.0 mm | 1.1 mm | 71% | 0.25 S/cm | 0.05 mm | 70 mA |
| Comparative Example 5 | 2.0 mm | 4.0 mm | 0.6 mm | 0.6 mm | 45% | 0.25 S/cm | 1.0 mm | 70 mA |

Example 2

A device for producing an organic hydride of Example 2 had the same configuration as in Example 1 except that as an anode substrate, an expanded mesh having a distance Comparative Example 3

A device for producing an organic hydride of Comparative Example 3 had the same configuration as in Example 1 except that as an anode substrate, an expanded mesh having a distance between centers in a short direction of 3.0 mm, a distance between centers in a long direction of 3.5 mm, a plate thickness of 1.0 mm, a pitch width of 1.1 mm, and an aperture ratio of 20% was used (see Table 1).

Comparative Example 4

A device for producing an organic hydride of Comparative Example 4 had the same configuration as in Example 1 except that as an anode substrate, an expanded mesh having a distance between centers in a short direction of 8.0 mm, a distance between centers in a long direction of 12 mm, a plate thickness of 1.0 mm, a pitch width of 1.1 mm, and an aperture ratio of 71% was used (see Table 1).

Comparative Example 5

A device for producing an organic hydride of Comparative Example 5 had the same configuration as in Example 2 except that a gap between the electrolyte membrane and the anode was 1.0 mm (see Table 1).
(Performance Evaluation)

Figure 3:
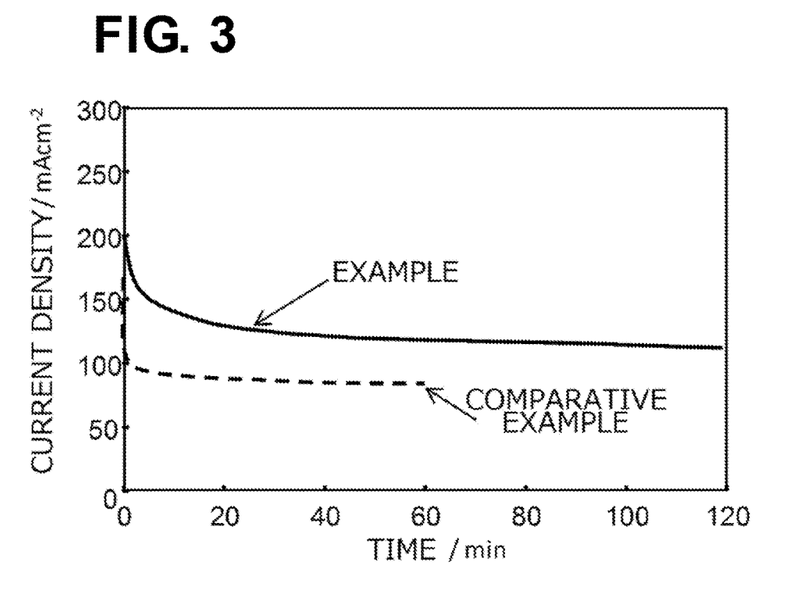
FIG. 3 is a graph showing a change with time of a current density in a device for producing an organic hydride of Example 1 in which 1.7 V is applied between an anode and a cathode and a change with time of a current density in a device for producing an organic hydride of Comparative Example 1 in which 1.75 V is applied between an anode and a cathode.

FIG. 3 shows a change with time of a current density in the device for producing an organic hydride of Example 1 in which 1.7 V was applied between the anode and the cathode by a constant voltage power supply and a change with time of a current density in the device for producing an organic hydride of Comparative Example 1 in which 1.75 V was applied between the anode and the cathode by the constant voltage power supply. Although the voltage between the anode and the cathode in Example 1 was lower than that in Comparative Example 1, a current density higher than that in Comparative Example 1 was obtained. In Comparative Example 1, a large decrease in voltage at the early stage was confirmed, and from the observation after complement of the test, remained bubbles in the Ti fiber-sintered sheet were confirmed. On the basis of this finding, it is considered that in Example 1, an oxygen gas generated on the anode side did not remain in the vicinity of the electrode and delivered to the upper portion, as compared with Comparative Example 1, and thus, a high current density was obtained even at a low interpolar voltage without an increase in overvoltage mainly caused by gas blocking on the anode side. In Example 1, instantaneous generation of hydrogen due to unstable electric potential on the cathode side (a decrease in Faraday effect against reduction of the organic substance) was not confirmed, and it was confirmed that a cathode reaction favorably proceeded due to a favorable anode state in an electrolysis reaction.

In each of the devices for producing an organic hydride of Examples 2 to 5 and Comparative Examples 2 to 4, 1.7 V was applied between the anode and the cathode by the constant voltage power supply, and after 60 minutes, the current density was measured. The current density obtained in each of the devices for producing an organic hydride is shown in Table 1.

In each of the devices for producing an organic hydride of Examples 1 to 4, a significant increase in the current density after 60 minutes as compared with Comparative Example 1 was confirmed.

When the gap was not provided between the electrolyte membrane and the anode, like Comparative Example 2, a decrease in the current density as compared with Example 1 was confirmed.

When the aperture ratio of the expanded mesh was out of a range of 30 to 70%, like Comparative Examples 3 and 4, it was confirmed that sufficient current density was not obtained.

When the gap between the electrolyte membrane and the anode was 1.0 mm, like Comparative Example 5, the gap was too large, and it was confirmed that sufficient current density was not obtained.

The present invention is not limited to the above-mentioned embodiments, and various modifications such as a design change may be added thereto on the basis of knowledge of those skilled in the art. Any embodiment to which such modifications are added may also be included in the scope of the present invention.

REFERENCE SIGNS LIST 10 device for producing organic hydride
11 electrolyte membrane
12 anode
13 cathode catalyst layer
14 cathode diffusion layer
15 cathode-membrane joined body
16a partition plate
16b partition plate
17a spacer
17b spacer
19 acidic electrolytic solution inlet
20 acidic electrolytic solution outlet
21 substance-to-be-hydrogenated inlet
22 hydride outlet
23 anode-supporting elastic body
24 cathode support
25 anode spacer
26 anode chamber
27 cathode chamber

INDUSTRIAL APPLICABILITY

The present invention can be applied to a device for producing an organic hydride in which hydrogenation of the organic hydride is electrochemically performed.

The invention claimed is:
1. A device for producing an organic hydride comprising:
a solid polymer electrolyte membrane having proton conductivity;
a cathode that is provided on a surface of the solid polymer electrolyte membrane and contains an electrolytic-hydrogenation catalyst for reducing a substance to be hydrogenated to produce a hydride;
a cathode chamber that accommodates the cathode and into which the substance to be hydrogenated is supplied;
an anode that is provided above another surface of the solid polymer electrolyte membrane and contains an electrode catalyst for oxidizing water to produce protons; and
an anode chamber that accommodates the anode and into which an electrolytic solution is supplied, wherein
a gap is formed between the anode and the electrolyte membrane,
wherein the electrode catalyst includes a solid solution of iridium oxide and tantalum oxide,
wherein the anode has a network structure with an aperture ratio of 30 to 70%, and has an electrical supply supporting material formed of an electronic conductor and the electrode catalyst held by the electrical supply supporting material, wherein the anode has a rhombic aperture shape with a distance between centers in a short direction of 0.1 to 4 mm and a distance between centers in a long direction of 0.1 to 6 mm, and wherein the gap is 0.02 to 0.2 mm.

2. The device for producing an organic hydride according to claim 1, wherein the electrolytic solution is any of sulfuric acid, phosphoric acid, nitric acid, and hydrochloric acid, which has an ion conductance measured at 20° C. of 0.01 S/cm or more.

3. The device for producing an organic hydride according to claim 1, wherein a gap is provided between the anode and the solid polymer electrolyte membrane.

4. The device for producing an organic hydride according to claim 1, wherein an spacer is disposed between the anode and the solid polymer electrolyte membrane.

* * * * *